United States Patent [19]

Knight et al.

[11] Patent Number: 4,894,062
[45] Date of Patent: Jan. 16, 1990

[54] STAKING ANCHOR FOR SOFT IOL

[75] Inventors: Patrica M. Knight, Laguna Niguel; Vladimir Portnoy, Irvine; F. Richard Christ, Orange; Alan E. Alosio, El Toro; Stanley L. Van Gent, Irvine; Lyle E. Paul, El Toro, all of Calif.

[73] Assignee: Allergan, Inc., Irvine, Calif.

[21] Appl. No.: 279,439

[22] Filed: Dec. 2, 1988

Related U.S. Application Data

[62] Division of Ser. No. 804,674, Dec. 4, 1985, Pat. No. 4,834,751.

[51] Int. Cl.⁴ .............................................. A61F 2/16
[52] U.S. Cl. ........................................................ 623/6
[58] Field of Search ........................ 623/6; 264/1.1, 1.7

[56] References Cited

U.S. PATENT DOCUMENTS

| | | | |
|---|---|---|---|
| 3,866,249 | 2/1975 | Flom | 623/6 |
| 4,150,471 | 4/1979 | Richards et al. | 264/1.7 X |
| 4,468,820 | 9/1984 | Uhler et al. | 623/6 |
| 4,547,914 | 10/1985 | Castleman | 623/6 |
| 4,573,998 | 3/1986 | Mazzocco | 623/6 |
| 4,615,702 | 10/1986 | Koziol et al. | 623/6 |
| 4,668,446 | 5/1987 | Kaplan et al. | 623/6 X |
| 4,737,322 | 4/1988 | Bruns et al. | 264/1.7 |

FOREIGN PATENT DOCUMENTS

| | | | |
|---|---|---|---|
| 4238478 | 6/1981 | Australia. | |
| 0125361 | 11/1984 | European Pat. Off.. | |
| WO84/00883 | 3/1984 | PCT Int'l Appl. | 623/6 |
| WO84/04881 | 12/1984 | PCT Int'l Appl. | 623/6 |

Primary Examiner—Ronald L. Frinks
Attorney, Agent, or Firm—Gordon L. Peterson

[57] ABSTRACT

An intraocular lens comprising a deformable optic and first and second fixation members. Each of the fixation members has a proximal end portion. First and second elongated anchors are coupled to the proximal end portions of the fixation members, respectively, and the anchors and the proximal end portions are within peripheral regions of the optic so that the anchors can assist in attaching the fixation members to the optic. The anchors are spaced apart so that the deformable optic can be folded to facilitate insertion of the optic through a relatively small incision into the eye.

6 Claims, 1 Drawing Sheet

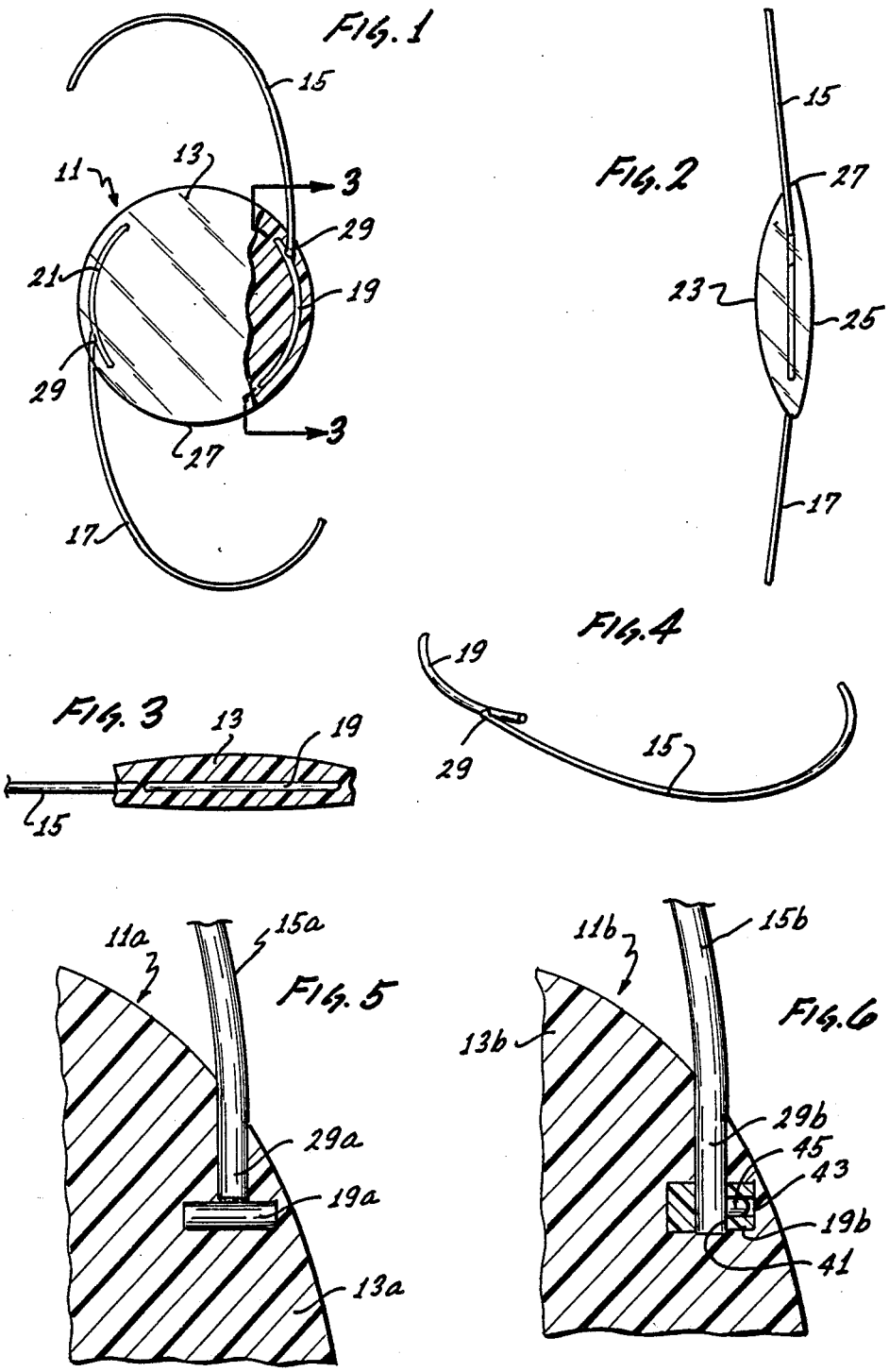

STAKING ANCHOR FOR SOFT IOL

This application is a division of application Ser. No. 804,674 filed on Dec. 4, 1985, now U.S. Pat. No. 4,834,751.

BACKGROUND OF THE INVENTION

Intraocular lenses (IOL's) are a well-known type of surgical implant used to replace the natural lens of an eye which has been damaged as a result of trauma or disease. Such IOL's typically comprise an optic and at least one fixation member attached to the optic. The fixation member functions to position the optic in the correct optical alignment within the eye. Many fixation members are of filamentary form, and are attached to the optic at or near the periphery of the optic.

It is conventional practice to construct the optic of a hard biocompatible polymer, such as polymethylmethacrylate (PMMA). More recently, it has been proposed to construct the optic from a relatively flexible or deformable material. When so constructed, the optic can be rolled or flexed into a relatively small cross-sectional configuration to permit it to be inserted through a relatively small incision into the eye to thereby reduce the trauma and likelihood of infection from the surgery.

The fixation members are constructed of a resilient material, typically polypropylene. In some IOL'S, the fixation members are integrally formed with the optic. In other types of IOL'S, various methods of attached the fixation members to the optic have been devised.

A common method of attaching requires drilling two small intersecting holes in the edges portion of the optic. A proximal end portion of the fixation member is inserted into one hole and a heated rod is inserted through the other of the intersecting holes. The heated rod melts the proximal end portion of the fixation member where contacted causing the melted material to flow into the second intersecting hole to form a mechanical interlock when the material solidifies. Great precision is required in the drilling of the intersecting holes. Also characteristic of the IOL'S made according to this method is the potential of debris-trapping cavities remaining from a less-than-complete filling of the holes in the optic by the melted portion of the fixation member.

The attachment of the fixation members to the optic is particularly troublesome when the optic is constructed of soft or deformable materials, such as silicone. When the deformable optic is folded or rolled prior to insertion through the incision into the eye, flexure of the optic creates a likelihood that the fixation member will become detached from the optic. If this occurs, it not only renders the IOL useless, but also is a potential hazard to the patient. The soft optic materials, such as silicone, do not have sufficient rigidity to be used as an integral fixation member or haptic.

It is known to attach the fixation members to a large resilient, circular ring and to mold the soft optic material over the ring so that the ring is concentric with the optic and extends along a peripheral region of the optic. However, for foldable optics, this construction precludes the use of rigid or non-foldable materials for the ring and requires the dedication of a large diameter annulus of the optic to capture the ring.

SUMMARY OF THE INVENTION

This invention improves the attachment of the fixation members to a soft or deformable optic and eliminates the ring of the prior art in favor of first and second elongated anchors or supports which are coupled to the proximal end portions of first and second fixation members, respectively. The anchors and proximal end portions are within peripheral regions of a deformable optic so that the anchors assist in attaching the fixation members to the optic. The anchors are spaced apart so that the deformable optic can be folded to facilitate insertion of the optic through a relatively small incision into the eye.

Because the anchors are spaced apart, they do not interfere with folding of the deformable optic. Accordingly, the anchors may be constructed of resilient material, rigid material, material which is more rigid than the material of the optic, or virtually any material suitable for placement within the optic. Also, the anchors can be much smaller than the ring of the prior art and thereby require much less dedicated space within the optic to accommodate them.

The anchors can be of various different constructions. For example, each of the anchors may include a filament which is molded integrally with the associated fixation member or formed separately and attached thereto as by welding or staking. The anchors may be of the same or different materials than the optic and the fixation members. By elongated the anchors, they can form a strong mechanical interlock with the optic and can hold the fixation members against rotation relative to the optic.

So as to best serve as an anchor, each of the anchors preferably extends away from the axis of the associated fixation member at the location where the anchor is coupled to the fixation member. For example, each of the anchors may include a filament which forms a segment of an arc and/or which extends generally transverse to the proximal end portion of the associated fixation member. In one preferred construction, the filament is elongated, forms the segment of an arc and is more rigid than the deformable optic so that it can provide a frame or skeleton to support the soft optic so as to decrease the likelihood that the optical properties of the optic will be altered when the IOL is introduced into the eye.

The invention, together with additional features and advantages thereof may best be understood by reference to the following description taken in connection with the accompanying illustrative drawing.

BRIEF DESCRIPTION OF THE DRAWING

FIG. 1 is an elevational view partially in section of one form of IOL constructed in accordance with the teachings of this invention.

FIG. 2 is a side elevational view of the IOL.

FIG. 3 is a fragmentary sectional view taken generally along line 3—3 of FIG. 1.

FIG. 4 is an isometric view of one form of fixation member and anchor.

FIGS. 5 and 6 are fragmentary sectional views illustrating portions of optics and fixation members being utilized with anchors of different configurations.

DESCRIPTION OF THE PREFERRED EMBODIMENTS

FIG. 1 shows an IOL 11 which comprises an optic 13 of a transparent, biocompatible material, fixation members 15 and 17 and anchors 19 and 21. Although the optic 13 could be of various different configurations, in the embodiment illustrated, it has a convex anterior face 23 (FIG. 2), a convex posterior face 25, and a cylindrical periphery or edge 27. The optic 13 is constructed of a suitable, soft, deformable material, such as silicone or polyurethane which permits the optic to be rolled or folded into a smaller configuration for insertion through a relatively small incision into the eye.

The fixation members 15 and 17 retain or fix the optic 13 in the correct position within the eye. Each of the fixation members 15 and 17 is in the form of an elongated, resilient strand or filament. Although the fixation members can be of various different configurations, in this embodiment, they are each constructed of a generally J-shaped configuration, and they are constructed of a resilient, biocompatible material, such as polypropylene.

Although the anchors 19 and 21 can be of various different configurations, in the embodiment of FIGS. 1–4, each of them is in the form of an elongated filament which forms a segment of an arc and which extends away from the axis of the associated fixation member. In this embodiment, the anchors 19 and 21 are of identical construction, although this is not essential. Each of the anchors 19 and 21 is joined to the associated fixation member 15 and 17 at a location spaced from the center of the segment of the arc. The anchors 19 and 21 may be constructed of any suitable biocompatible material, such as polymethylmethacrylate (PMMA), which is quite rigid, or polypropylene, which is relatively resilient. In either case in this specific embodiment, the anchors 19 and 21 are more rigid than a silicone or polyurethane deformable optic 13. The anchors 19 and 21 may be molded integrally with the fixation members 15 and 17 or they may be formed separately and attached to the proximal end portions 29 as by welding or staking.

Although the length of the arcs formed by the anchors 19 and 21 can vary, in this embodiment, each of the anchors extends for about 90 degrees. The anchors 19 and 21, in this embodiment, are diametrically opposite and are spaced apart by approximately 90 degrees. The anchors 19 and 21 are coupled to proximal end portions 29 of the fixation members 15 and 17, respectively. The anchors 19 and 21 and the proximal end portions 29 are within peripheral regions of the optic 13, and the anchors are closely adjacent the periphery 27. In addition, the anchors 19 and 21 are preferably concentric with the optic 13. The optic 13 is cast or molded over the proximal end portions 29 and the anchors 19 and 21.

This construction provides important advantages. For example, the anchors 19 and 21 form a strong mechanical interlock with the optic 13 which not only prevents withdrawal of the fixation members 15 and 17 from the optic, but also prevents rotation of the fixation members relative to the optic. In addition, because the opposite ends of the anchors 19 and 21 are widely spaced, the anchors do not interfere with folding or rolling of the optic 13 into a smaller configuration for insertion through a relatively small incision into the eye. Accordingly, even if the anchors 19 and 21 are constructed of rigid material, the optic 13 can still be folded for insertion through the small incision. Also, the anchors 19 and 21 serve as supports to support the deformable optic 13 so as to decrease the likelihood that the optical properties of the optic will be altered when the IOL is introduced into the eye.

FIGS. 5 and 6 show IOL'S 11a and 11b, respectively, and each of these IOL'S is identical to the IOL 11 in all respects not shown or described herein. Portions of the IOL'S 11a and 11b corresponding to portions of the IOL 11 are designated by corresponding reference numerals followed by the letters "a" and "b", respectively.

The IOL'S 11a and 11b differ from the IOL 11 in the construction of the anchors 19a and 19b. Each of the anchors 19a and 19b is in the form of an elongated rod, plate filament or plug of a suitable plastic, such as PMMA or polypropylene. Both of the anchors 19a and 19b extend generally transverse to the associated proximal end portions 29a and 29b. The anchor 19a is welded to the proximal end portions 29a, and the anchor 19b is staked to the proximal end portion 29b. More specifically, the staking may be carried out, for example, by inserting a region of the proximal end portion 29b into or through a hole 41 of the anchor 19b and inserting a hot rod through a bore 43 to melt a portion of the proximal end portion 29b and form a projection 45 in the bore 43 which interlocks with the bore to attach the anchor 19b to the proximal end portion 29b. Following the attachment of the anchors 19a and 19b, the optics 13a and 13b are molded, respectively, about the proximal end portions 29a and 29b and the anchors.

The anchors 19a and 19b interlock with the material of the associated optics 13a and 13b to provide a strong mechanical interlock. In addition, the anchors 19a and 19b prevent rotation of the associated fixation members 15a and 15b relative to the optic. Of course, additional fixation members can be attached to the optics 13a and 13b in accordance with the principles of this invention.

Although exemplary embodiments of the invention have been shown and described, many changes, modifications and substitutions may be made by one having ordinary skill in the art without necessarily departing from the spirit and scope of this invention.

We claim:
1. An intraocular lens comprising:
   an optic which is deformable to facilitate insertion of the optic through an incision into the eye;
   first and second fixation members, each of said fixation members having a proximal end portion;
   first and second anchors coupled to the proximal end portions of the first and second fixation members, respectively, at least one of said anchors including a filament extending transversely on both sides of the associated fixation member at the location where said one anchor is coupled to such fixation member, said filament being substantially perpendicular to the associated fixation member at said location;
   said optic being molded over said anchors and said proximal end portions;
   said anchors and proximal end portions being within peripheral regions of the optic whereby the anchors assist in attaching the fixation members to the optic; and
   said anchors being spaced apart whereby the deformable optic can be folded to facilitate insertion of the optic through an incision into the eye.

2. An intraocular lens as defined in claim 1 wherein each of said anchors is rigid.

3. An intraocular lens as defined in claim 1 wherein said filament of said one anchor is welded to the associated fixation member.

4. An intraocular lens as defined in claim 3 wherein said anchors are rigid.

5. An intraocular lens as defined in claim 1 wherein each of said anchors is more rigid than the optic.

6. An intraocular lens comprising:
an optic which is deformable to facilitate insertion of the optic through an incision into the eye;
first and second fixation members, each of said fixation members having a proximal end portion;
a first anchor coupled to the proximal end portion of the first fixation member;
a second anchor having a hole receiving a region of the proximal end portion of the second fixation member;
means for attaching said second anchor to the proximal end portion of the second fixation member, said second anchor extending transversely on both sides of the second fixation member at the location where said second anchor is coupled to the second fixation member;
said optic being molded over said anchors and said proximal end portions;
said anchors and proximal end portions being within peripheral regions of the optic whereby the anchors assist in attaching the fixation members to the optic; and
said anchors being spaced apart whereby the deformable optic can be folded to facilitate insertion of the optic through an incision into the eye.

* * * * *

UNITED STATES PATENT AND TRADEMARK OFFICE
CERTIFICATE OF CORRECTION

PATENT NO. : 4,894,062

DATED : January 16, 1990

INVENTOR(S) : Patricia M. Knight et al

It is certified that error appears in the above-identified patent and that said Letters Patent is hereby corrected as shown below:

On the title page, under item [19], "Knight" should be --Christ--;

The following inventors should be deleted from the patent in item [75]:

"Patricia M. Knight
Vladimir Portnoy
Alan E. Alosio".

Column 1, line 31 change "attached" to -- attaching --.

Column 2, line 32 change "elongated" to -- elongating --.

Signed and Sealed this

Nineteenth Day of March, 1991

Attest:

HARRY F. MANBECK, JR.

*Attesting Officer*  *Commissioner of Patents and Trademarks*